United States Patent [19]

Spears

[11] Patent Number: 5,344,419
[45] Date of Patent: Sep. 6, 1994

[54] APPARATUS AND METHOD FOR MAKING A DIFFUSING TIP IN A BALLOON CATHETER SYSTEM

[75] Inventor: James R. Spears, Bloomfield Hills, Mich.

[73] Assignee: Wayne State University, Detroit, Mich.

[21] Appl. No.: 52,368

[22] Filed: Apr. 23, 1993

[51] Int. Cl.$^5$ .............................................. A61B 17/36
[52] U.S. Cl. ...................................... 606/15; 606/17; 606/7
[58] Field of Search ...................... 606/2, 3, 7, 13–17; 128/395–398

[56] References Cited

U.S. PATENT DOCUMENTS

| | | | |
|---|---|---|---|
| 4,799,479 | 1/1989 | Spears | 606/15 |
| 5,041,109 | 8/1991 | Abela | 606/15 |
| 5,151,096 | 9/1992 | Khoury | 606/17 |
| 5,193,526 | 3/1993 | Daikuzono | 606/7 X |
| 5,196,005 | 3/1993 | Doiron et al. | 606/7 |
| 5,207,669 | 5/1993 | Baker et al. | 606/7 |
| 5,219,346 | 6/1993 | Wagnieres et al. | 606/17 |

*Primary Examiner*—Peter A. Aschenbrenner
*Attorney, Agent, or Firm*—Brooks & Kushman

[57] ABSTRACT

An apparatus and method are disclosed for making a laser balloon catheter (10) having a diffusing tip (24) for propagating a uniform cylindrical pattern of laser energy. Included in the catheter are an elongated flexible tube (12) with an inflatable balloon (14) connected to the tube and means for inflating (16) and deflating (18) the balloon. A central channel (20) is disposed within the balloon and coupled to the tube. An optical fiber (22) with the diffusing tip at its distal end delivers laser radiation through the balloon to tissue to be treated. The method comprises the steps of etching the distal end of the optical fiber to form an etched portion thereof, cladding the etched portion with a medium which secures the optical fiber to the central channel, and microballoons which diffuse the laser radiation radially from the optical fiber, thereby substantially avoiding axial propagation and heating of blood forward of the optical fiber.

21 Claims, 1 Drawing Sheet

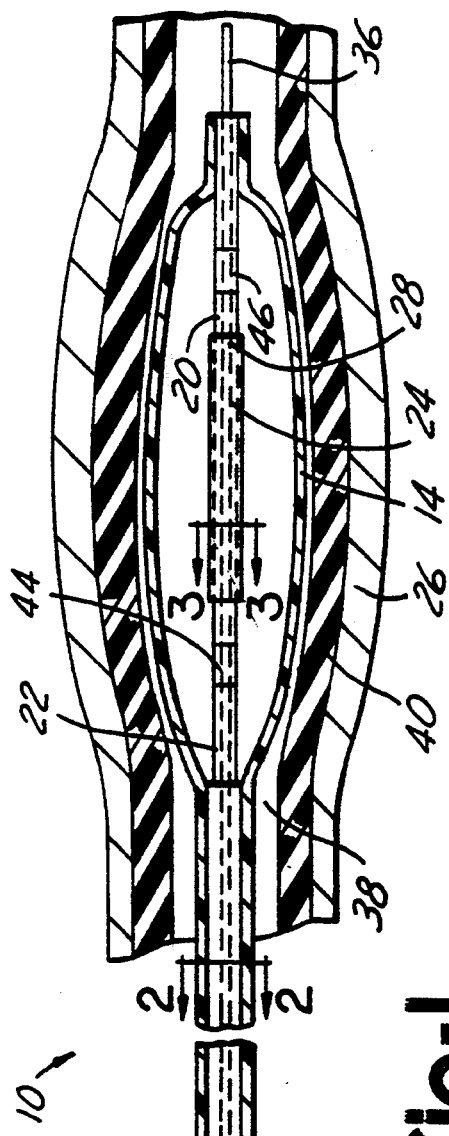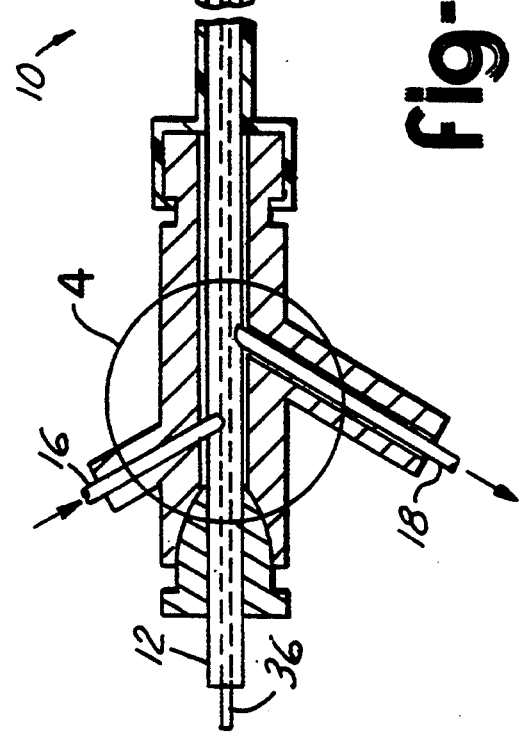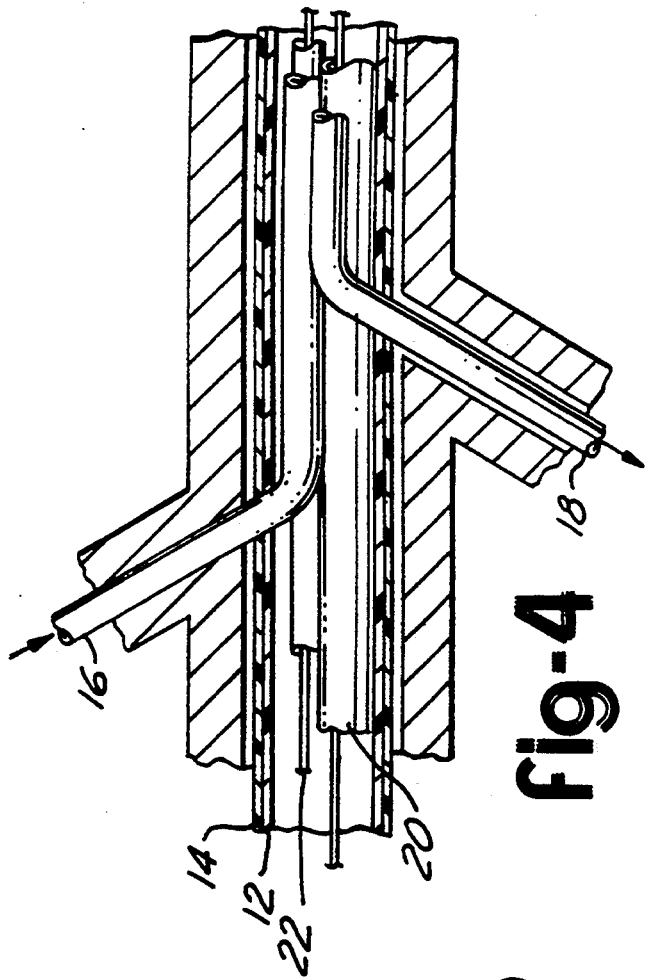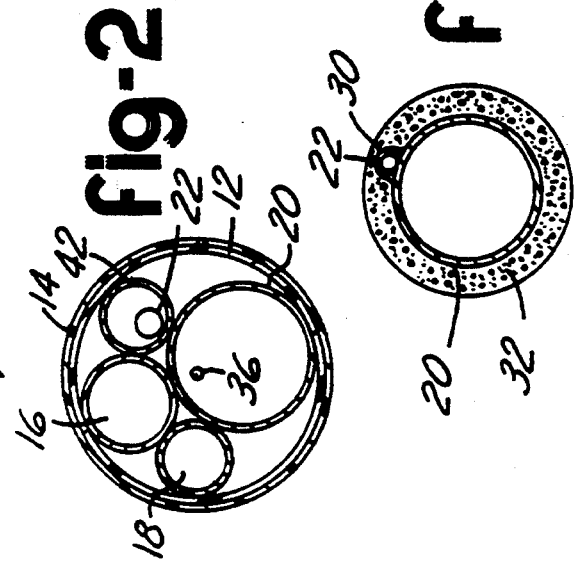

APPARATUS AND METHOD FOR MAKING A DIFFUSING TIP IN A BALLOON CATHETER SYSTEM

STATEMENT OF FEDERALLY SPONSORED RESEARCH

The funding for work described herein was provided in part by the Federal Government, under a grant from the National Institute of Health. The government may have certain rights in this invention.

TECHNICAL FIELD

This invention relates to angioplasty, and more particularly to a laser balloon catheter having a diffusing tip which provides a cylindrical dispersion of electromagnetic radiation at high power from the distal end of a fiberoptic which is flexible and resistant to damage.

BACKGROUND ART

One of the most promising non-surgical artery-clearing procedures to emerge in recent years is angioplasty. The procedure calls for the use of a small inflatable balloon which dilates a narrowed artery and removes blockage. A catheter having an inflatable balloon secured to its distal end is advanced through an artery to a narrowed region. The balloon is then inflated with a fluid from an external source, causing the narrowed region of the artery to be expanded. The balloon is then inflated and withdrawn. However, the procedure creates arterial damage of its own which may cause the artery to narrow within three to six months in as many as 50% of successfully treated patients. If narrowing occurs, the patient may develop similar symptoms and risks again. Accordingly, the need has arisen to reduce angioplasty-induced lesions.

A technique which has shown promise for overcoming the problems of restenosis is the simultaneous application of heat and pressure to a plaque-narrowed region of an artery. In such techniques, a catheter having an inflatable balloon at its distal end is advanced to a narrowed region of an artery. The balloon is inflated, as in the case of conventional balloon angioplasty. However, in contrast to conventional balloon angioplasty, sufficient heat is applied through the wall of the balloon to fuse the surrounding tissue and thereby eliminate flaps which can later block an artery. One useful means of heating the surrounding tissue is by directing laser radiation through an optical fiber carried by the catheter and terminating within the balloon. The laser radiation is then directed through the balloon wall to cause heating of the surrounding tissue.

An earlier high power, helical, flexible diffusing tip was invented by Spears et al., U.S. Pat. No. 4,878,492, issued Nov. 7, 1989, and was used in the first clinical laser balloon angioplasty system disclosed in U.S. Pat. No. 4,799,479, also issued to the present inventor on Jan. 24, 1989. The disclosures of each of these patents are incorporated herein by reference.

Previously known designs of the diffusing tip, however, do not provide a cylindricalty symmetrical pattern of dispersion of fiberoptically-delivered laser energy. In addition, control of the axial propagation of radiation is difficult and unpredictable during fabrication of the diffusing tip, so that many diffusing tips are either inappropriately long or short. Moreover, the diffusing tip is relatively bulky, stiff, and prone to fracture.

Excessive radiation, particularly at the distal end of the diffusing tip, has necessitated the use of a highly reflective gold coating at the proximal and distal cone ends of the balloon surrounding the diffusing tip in order to prevent inadvertent heating of blood in contact with the balloon at these locations. But such an apparatus is only partially effective and expensive to fabricate.

Furthermore, the central channel and the guidewire within the central channel are exposed to a high dose laser energy. This has resulted in thermal shrinkage of the polyethylene central channel and bonding of the latter to the guidewire.

Thus, a diffusing tip which provides cylindrically symmetric dispersion of electromagnetic radiation at high power from the distal end of a fiberoptic, yet is flexible and resistant to damage at high power, has not been previously available.

SUMMARY OF THE INVENTION

The method aspect of the present invention is used to make a laser balloon catheter with an elongated flexible tube which has an inflatable balloon secured thereto. Means for inflating and deflating the balloon are provided. A central channel is disposed in the balloon and is coupled to the tube. An optical fiber with a diffusing tip at its distal end delivers radiation through the tube and the balloon to tissue to be treated.

The method comprises the steps of: etching the distal end of the optical fiber to form an etched portion thereof, and cladding the etched portion with an adhesive translucent medium which secures the optical fiber to the central channel. Further, the method comprises the steps of applying to the translucent medium another coating which surrounds the central channel, the coating having suspended therewithin a plurality of microballoons for diffusing the laser radiation radially from the optical fiber without shadowing by the central channel, thereby substantially avoiding axial propagation and heating of blood forward of the optical fiber.

Preferably, the cylindrically uniform, flexible, hollow diffusing tip for high power laser energy dispersion is made by etching the silica cladding of a silica clad/silica core fiberoptic etched at its distal end in hydrofluoric acid. The etched portion of the fiberoptic is then reclad with a bonding medium such as a flexible, transparent epoxy which bonds the etched portion to the hollow polymeric tube.

Without further modification, laser radiation would propagate strongly in a forward direction, despite the lateral loss into and through the epoxy. However, on the external surface of the layer of epoxy, a second coating of the epoxy is applied, within which glass microballoons are suspended.

By applying a layer of epoxy around the entire circumference of the hollow polymeric tube, propagation of radiation is achieved uniformly about the tube's circumference, and the direction of the radiation no longer has a strong forward component.

Accordingly, it is a general object of the present invention to provide an improved laser balloon catheter.

It is a further object of the present invention to provide a laser balloon catheter capable of delivering and surviving a high power output.

It is yet another object of the present invention to provide a laser balloon catheter which produces substantially uniform heating of tissue surrounding the balloon.

It is still yet another object of the present invention to provide a method for manufacturing a laser balloon catheter.

It is an additional object of the present invention to provide a laser balloon catheter wherein heat dissipation of laser radiation with the balloon is limited to localized, radial heating deep into an arterial wall without excessive total energy.

It is a further object of the present invention to provide a laser balloon catheter wherein a relatively high proportion of the laser radiation is delivered through the balloon wall to surrounding tissue without significant axial propagation.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1 is a cross-sectional view of an anatomical environment and apparatus used to practice the present invention, in which an area immediately surrounding an inflated balloon may be permeated by a bioprotective material and bonded by thermal energy delivered thereto within the arterial wall being treated;

FIG. 2 is a cross-section of the laser balloon angioplasty catheter along the line 2—2 of FIG. 1;

FIG. 3 is a cross-section of the laser balloon angioplasty catheter along the line 3—3 of FIG. 1; and FIG. 4 is an enlarged view of the encircled area of FIG. 1.

BEST MODE FOR CARRYING OUT THE INVENTION

Overall, the disclosed laser balloon angioplasty system comprises the following main components:

1. A laser balloon angioplasty catheter with a transparent, high temperature (e.g. polyethylene terephthalate (PET)) balloon and an optical diffusing tip, which will be discussed in more detail below;

2. A laser system which provides continuous wave laser radiation at 1.06 microns which is coupled to a fiberoptic in the laser balloon catheter via a fiberoptic jumper connected directly to the laser;

3. (Optionally) A heparin film on the balloon. The film is a bioprotective material which may be fused to an arterial wall which is injured during angioplasty; and 4. (Optionally) A sheath within which the laser balloon catheter is temporarily placed, which prevents premature wash-out of the bioprotective material applied to the surface of the balloon before advancement of the balloon beyond the sheath to the coronary segment of interest.

The present invention discloses an apparatus and method for making the optical diffusing tip of the laser balloon angioplasty catheter noted above.

Referring to FIGS. 1-4 of the drawings, there is depicted a laser balloon catheter 10 and an elongated flexible tube 12. Connected to the tube 12 is an inflatable balloon 14. Means for inflating 16 and deflating 18 the balloon 14 are also provided. Disposed within the tube 12 is a central channel 20 which extends within the balloon 14. An optical fiber 22 extends axially through the tube 12 and balloon 14. The optical fiber 22 has a diffusing tip 24 at its distal end for delivering laser radiation through the balloon 14 to tissue 26 to be treated.

The method of the present invention comprises the steps of: etching the distal end of the optical fiber 22 to form an etched portion 28 thereof, and cladding the etched portion with an adhesive translucent medium which secures the optical fiber to the central channel. Further, the method calls for applying to the medium another coating which surrounds the central channel. The coating has suspended therewithin a plurality of microballoons for diffusing the laser radiation radially from the optical fiber, thereby substantially avoiding axial propagation and heating of blood forward of the optical fiber.

The distal end of the optical fiber 22 thus forms an etched portion 28 thereof. The bonding medium 30 (FIG. 3) secures the optical fiber 22 to the central channel 20. The coating 32 of suspending medium is applied to the bonding medium 30. If desired, the bonding medium and the suspending medium may be of the same substance, such as an epoxy. Additionally, if desired, application of the bonding and suspending medium may be applied in one step.

In one embodiment, the coating 32 has suspended therewithin a plurality of microballoons 34 for diffusing the laser radiation radially from the optical fiber 22 without the central channel 20 eclipsing laser energy. This substantially avoids axial propagation and unwanted heating of blood forward of the optical fiber 22 and distal to the balloon 14.

Additional details will now be provided of the preferred method steps and structural features of the disclosed laser balloon catheter system.

The diffusing tip 24 is preferably mounted on a 5-10 mm long section of polyimide tubing 20. The system allows performance not only of laser balloon angioplasty, but also the use of laser radiation to induce adherence of a wide variety of drugs or drug carriers to the luminal surface of arteries and other tubular soft tissue structures.

The basic components of the system consist of a movable guidewire 36, the balloon catheter 10 with the diffusing tip 24, and a sheath 40 (FIG. 1) which protects drugs or drug carrier(s) 38 trapped between the sheath 40 and surface of the deflated balloon 14 from premature dissolution prior to deployment. FIG. 1 depicts the sheath 40 within which the laser balloon catheter 10 is temporarily placed. The sheath 40 prevents premature wash-out of the bioprotective material 38 applied to the surface of the balloon 14 before advancement of the balloon beyond the sheath 40 to the coronary segment of interest.

In practice, the sheath 40 is removed no more than about one minute before the juxtaposition of the bioprotective material 38 to the tissue 26 to be treated.

The body of the balloon catheter comprises four polyimide tubings (FIG. 2) in parallel surrounded by a polyester heat-shrink tubing 12. The central channel 20 passage of the guidewire 36 is a 0.020 inch i.d., 0.022 inch o.d. tubing. The balloon inflation/deflation channel 16 is a 0.012 inch i.d., 0.014 inch o.d. tubing. An additional deflation channel 18 is a 0.010 inch i.d., 0.011 inch o.d. tubing. The fourth channel is a 0.010 inch, 0.011 inch o.d. tubing for housing the silica core (105 millimeter o.d.)/silica clad fiberoptic (Spectran) having a polyimide buffer with an o.d. of 150 mm. The epoxy used to bond all four polyimide tubings together is highly flexible upon curing (Envirotex Lite). The outer jacket of the body of the catheter consists of polyester heat-shrink tubing 12 having a 0.011 inch wall thickness which is shrunk with a heat gun from an o.d. of 0.045 inches to a final o.d. of approximately 0.03 inches at temperatures (110° C.–130° C.) below the melting point of the polyimide tubing and epoxy. If desired, an additional layer 14 of heat-shrink polyester tubing (0.002 inch wall thickness) is shrunk over the proximal ⅔ of the catheter.

The tubes for balloon inflation 16 and deflation 18 terminate near the proximal cone end of the balloon.

For a coronary artery application, the preferred internal dimensions of the central channel 20 are 0.020" and those for the inflation/deflation channels are in the 0.008" to 0.010" range.

The balloon material is relatively noncompliant, such polyethylene terephthalate, so that balloon inflation at high distending pressures (e.g., 4–15 bar) does not cause the central channel 20 to shift from its centrally located position. The diffusing tip 24 therefore remains centrally located during balloon inflation. The preferred polyethylene terephthalate (PET) angioplasty balloon is manufactured by Advanced Polymers, Inc.

The advantage of this material or its equivalents is twofold. The polyethylene terephthalate balloon material is normally quite difficult to bond to many polymeric materials, but I have found that it can be easily and effectively bonded to polyimide with the use of Envirotex Lite epoxy. Also, the high temperature melting point of polyimide (as well as the only other internal component of the balloon shaft—the silica core and cladding of the fiberoptic) allows the use of heat shrink fluoropolymer tubing (e.g., TFE Sublite-Wall tubing from Zeus Industrial Products, Inc., Raritan, N.J.) as an outer jacket if desired. Such material requires high temperatures for thermal shrinkage, and therefore performs satisfactorily as an external protective jacket.

Although the melting point of the polyimide is actually lower than the temperature required for thermal shrinkage of the fluoropolymer tubing, a brief exposure of the external surface of the TFE tubing to a heat gun and/or protection of the polyimide tubing with cold water which can flow through the channels, prevents the polyimide tubing from melting.

The optical fiber or fiberoptic 22 preferably has a silica core of about 10 microns, and an external diameter of the buffer of less than 150 microns. Since a useful buffer material is polyimide, all internal components of the balloon catheter are either polyimide or are coated with this material.

While one optical fiber 22 is depicted in the drawings, it will readily be appreciated that more than one optical fiber 22 may be distributed around the circumference of the central channel 20. When this is the case, added uniformity of radial propagation is achieved.

The proximal end of the fiberoptic 22 is flat-cleaved, polished, and housed in a standard SNA connector. The distal end of the fiberoptic is etched in hydrofluoric acid over a desired length, such as 7 millimeters. After advancement of the fiberoptic beyond the distal end of its protective channel 42, it is epoxied to the outer surface of the central channel 20.

An additional coating 32 of the epoxy, having a thickness of 0.001 inch–0.004 inch, in which glass microballoons are embedded to facilitate scattering, is placed over the etched long segment of the central channel 20. A suitable epoxy for both layers 30, 32 is a bisphenol A resin/polyamine curing agent combination, such as Envirotex Lite. The low absorption of 1.06 millimeter Nd:YAG laser radiation by the epoxy and the microballoons allows high power transmission without significant thermal challenge to ambient materials.

If desired, two gold marker bands 44, 46 (FIG. 1) may be placed upon the central channel 20 one millimeter proximal and one millimeter distal to the diffusing tip 24. The central channel 20 with the pair of spaced-apart radial opaque markers 44, 46 can be seen in an X-ray. In this way, the laser balloon catheter 10 can be precisely located during use.

Laser energy delivered by the fiberoptic 22 is generated by a Quantronix System 1500 medical laser (cw Nd: Yag radiation at 1.06 micron wavelength). Operational details are omitted for brevity, and are considered to be within the knowledge of those of ordinary skill in the art.

Typically, after heat shrinking either the polyester tubing or the thin-walled fluoropolymer tubing 12 onto the polyimide channels 16, 18, 20 and fiberoptic 22, an external dimension of 3 French or less can be easily achieved. Once the proximal ends of the channels and fiberoptic are terminated appropriately and the balloon is epoxied in position, the balloon catheter can be used as a laser balloon catheter 10 after appropriate tests of its mechanical properties and laser-transmitting ability.

The pattern of electromagnetic radiation emitted is controlled by placement of the epoxy/microballoon slurry 32. Since the lateral dispersion of radiation can be observed with, for example, a reference helium-neon laser coupled to the fiberoptic 22, one can "paint" with light by brushing the uncured epoxy/microballoon slurry 32 on the first layer 30 of cured epoxy.

The glass microballoons serve to refract light at the glass/internal air interfaces and to a lesser extent, at the glass/epoxy interfaces, and are highly transparent to electromagnetic radiation over a wide range of wavelengths. The microballoons are highly efficient at converting forward propagating radiation to that of a radially random pattern.

The mean outside diameter of the microballoons is 0.001 to 0.002 inches and their wall thickness is about 0.0001 to 0.002 inches. The mass of microballoons used is typically less than 1 microgram, but their efficient scattering of electromagnetic radiation results in a cylindrical propagation pattern surrounding the central channel 20.

Transverse waveguiding of radiation about the inner and outer coating of epoxy occurs in a manner which results in little radiation being directed toward the lumen of the hollow polymeric tube 20. The presence of a material which strongly absorbs radiation, such as the guidewire 36 within the lumen therefore is only minimally heated. Accordingly, the need to cool the lumen with an injection of a crystalloid solution, as was required for previous clinical laser balloon systems, is greatly reduced or even eliminated.

The diffusing tip 24 fabricated in this manner is structurally an integral part of a section of the hollow polymeric channel 20. This design results in a diffusing tip which is highly flexible, has a low profile, is mechanically strong, and is cylindrically symmetrical. For these reasons, such a structure contrasts with the previously available diffusing tip 24 used for laser balloon angioplasty.

Although a wide variety of materials can be used for the hollow polymeric tube 12, a particularly attractive material is polyimide, since this material has: (a) a high tensile strength even for thin-walled tubes (e.g., 0.001"), (b) a high melting pint (ca. 200° C.), (c) its relatively dark color precludes any inadvertent forward propagation to the distal end of the balloon 14, and (d) the material has been used successfully to protect fiberoptics.

It should be noted that the diffusing tip 24 need not be fabricated on the external surface of the hollow polymeric tube 20. The latter is useful for balloon angioplasty procedures and facilitates passage of the guidewire 36 through the diffusing tip 24. For procedures not requiring the use of a guidewire, a solid polymeric tube would serve equally well. Although a ceramic, glass, or metallic tube could be used, polymeric tubes (hollow or solid) are preferred because of greater flexibility. In applications wherein a stiff support for the diffusing tip is attractive, these alternative materials could be used.

Although the previously described cylindrical optical diffusing tip allows excellent transmission of visible and near infrared wavelengths of light, strong absorption of ultraviolet wavelengths allows less than 10% of UV light to be emitted by the diffusing tip. A modification of the cylindrical diffusing tip allows use of ultraviolet wavelengths without excessive absorption of the latter.

A silica fiberoptic (e.g., 105 micron core, 125 micron silica clad, low OH fiberoptic from Spectran) is etched in hydrofluoric acid, after removing the buffer. A thin layer of a fluoropolymer paste is then applied to the etched surface of the fiberoptic which scatters UV light (and visible, IR light) in a radial direction typically along a 1-2 cm length. The fiberoptic is then sandwiched between two layers of thin-walled fluoropolymer tubing, the outer layer of which is heat shrinkable. After heat shrinking the outer tubing with a heat gun, the fiberoptic is essentially embedded in the wall of the combined two layers of tubing. Lateral waveguiding and the transparency of the fluoropolymer materials result in a cylindrical diffusing tip which absorbs less than 50% of radiation in the UV range.

For example, the proximal end of the silica fiberoptic within a 3.0 mm laser balloon catheter (polyethylene terephthalate balloon filled with water), within which the central shaft was fabricated from the fluoropolymer tubings, was connected to the UV output from an argon laser (250 mW output at principal lines of 351 nm and 363 nm), and a transmission efficiency of 50-60% was found across the diffusing tip and balloon by use of an integrating sphere.

An additional advantage in the use of the fluoropolymer paste and tubings is that, with sufficient heating, the etched portion of the fiberoptic is protected by recladding with a fluoropolymer, thereby conferring increased mechanical strength and a reduction in the brittleness of the fiberoptic. The fluoropolymer tubings, once heat shrunk together, functionally provide a single tube, the lumen of which allows passage of a guidewire.

In order to deliver a drug either directly or via a carrier (e.g., erythrocytes, albumin microspheres, and other biocompatible carriers), a solution or suspension of the drug or carrier may be applied to the external surface of the inflatable balloon 14 in its deflated state. The balloon catheter, which will have already advanced through the sheath 40 (FIG. 1), will then be withdrawn so that the deflated balloon with the drug or drug carrier is within the distal several centimeters of the sheath 40. Pressure within the balloon is then applied via the inflation and/or deflation channels 16, 18, thereby trapping the drug or carrier between the external balloon surface and inner surface of the sheath.

During the practice of laser balloon angioplasty with local drug delivery, the deflated balloon along with the entrapped drug or carrier and sheath are advanced together within a guide catheter over a guidewire previously advanced across a lesion of interest. When the operator is ready to perform laser balloon angioplasty, negative pressure is applied to the balloon, thereby allowing advancement of the balloon with the drug or carrier coating across the lesion. If the lesion is crossed and the balloon is inflated within approximately a minute after advancement beyond the sheath, blood flow past the deflated balloon will wash only a portion of the drug or carrier away from the surface of the balloon.

In many instances, conventional balloon angioplasty will be performed prior to laser balloon angioplasty, since crossing the lesion may be difficult and most of the drug or carrier would be lost before balloon inflation is attempted. However, laser balloon angioplasty could be performed initially without the drug or carrier to simply dilate the lesion and the procedure repeated subsequently to apply local drug therapy with heat.

Clinical applications for the diffusing tip include laser balloon angioplasty; photodynamic therapy; the use of light to elicit tissue fluorescence; the use of light for polymerization of light-cured epoxies; induction of adherence of drugs or drug carriers with light or heat produced by light exposure; deployment of polymeric stents with radiation-induced heating; and local hyperthermia treatment of diseased tissues.

The fabrication steps of the LBA catheter will now be described in additional detail. The steps are as follows.

1. Align five foot lengths of one 0.020" i.d. (0.022 o.d.) polyimide tubing, one 0.012" i.d. (0.014" o.d.), and two 0.010" i.d. (0.011 o.d.) polyimide tubings (Hudson International, medical grade) in parallel and epoxy together with Envirotex Lite epoxy. Check dimensional accuracy of each tubing (QC). The distal 2" and proximal 4" portions of the tubings are left free of epoxy. A 0.018" guidewire will have been positioned within the 0.002" i.d. tubing, which will serve as the central channel of the catheter, prior to application of epoxy.

2. Place a 2 foot length of polyester heat shrink tubing (Advanced Polymers: 0.043" i.d., 0.045" o.d.), after checking its dimensional accuracy (QC) over the proximal end of the epoxy-bonded 4 tubings and heat shrink with a heat gun. Then cover the entire epoxy-bonded length of the 4 tubings with a 4'6" length of 0.043" i.d. (0.044" o.d.) polyester heat shrink tubing and heat shrink with a heat gun. Remove the 0.018" guidewire and replace with a 0.014" guidewire for all subsequent steps.

3. Check the ease of wire movement and check both the outer diameter and uniformity of shrinkage of the polyester tubings.

4. Remove the distal 2 cm protective coating (polyimide, 150 micron o.d.) from a 105 micron silica core, 125 micron silica clad fiberoptic (Spectran) with hydrofluoric acid. Further etch the distal 5 mm of the fiberoptic to taper the end to <50 microns. Rinse the distal end of the fiberoptic in water.

5. Pass the fiberoptic through one of the 0.010" i.d. polyimide tubings, so that the distal end of the fiberoptic is extruded just beyond the distal end of the polyimide tubing. The proximal end of the fiberoptic will have been fitted with a standard stainless steel fiberoptic connector, polished flat, and the length of fiberoptic proximal to the polyimide tubing will have been jacketed with a medical grade micro-bore polyethylene tubing (Fisher, 0.050" i.d., 0.090" o.d.). The proximal end will have been inspected at >50×magnification for determination that the polished fiber is free of observable defects.

6. Epoxy the distal 12 mm of the fiberoptic to the outer surface of the central shaft with Envirotex Lite epoxy.

7. With a helium-neon laser coupled to the proximal end of the fiberoptic, coat the distal 7 mm of the fiberoptic with a thin film (<0.03") of a slurry of Envirotex Lite epoxy and glass microballoons (Emerson and Cumming, FTD 202 Eccospheres with an i.d. of 20–40 microns and a wall thickness of 2–4 microns) so that a cylindrically uniform pattern of light is evident.

8. Epoxy two 1 mm long gold marker bands (0.0235" i.d., 0.025" o.d.) to the central channel, 2 mm proximal and distal to the cylindrical diffusing tip, with Envirotex Lite epoxy.

9. Connect 3-way stop cocks to proximal ends of the 0.010" inflation/deflation channels with epoxy (within microbore polyethylene tubing) and PVC heat shrink tubing.

10. Connect luer-lock fitting to proximal end of central channel with heat shrink polyester tubing, epoxy, and PVC tubing.

11. Epoxy all 4 channels at the proximal end of the catheter within a rigid polycarbonate cone and heat shrink PVC tubing over the latter and adjacent proximal end of the catheter with the polyester tubing.

12. Attach polyethylene terephthalate balloon to the distal end of the catheter with Envirotex Lite epoxy. Cut distal extension to 5 mm beyond the balloon.

13. Check for ease of guidewire movement (either a 0.010", 0.012", or 0.014" guidewire) through the central shaft.

14. Inflate balloon to 10 bar and deflate via both the inflation and deflation channels to check for balloon integrity and function of the channels.

15. Deliver 20 watts cw Nd:YAG laser energy (1.06 micron wavelength) from the diffusing tip under water for 10 seconds, with the balloon inflated with sterile water at 4 bar, while flushing the central channel manually with sterile water, as a test of the integrity of the diffusing tip. Examine the helium-neon light pattern before and laser exposure. Catheters with diffusing tips which are less than 6 mm or greater than 8 mm in axial length will be rejected.

16. Flush central channel with a heparin-benzalkonium chloride solution (750 U heparin/ml; North American Science Associates, Northwood, Ohio); air dry; flush with sterile water; air dry.

17. Clean outside surfaces of the catheter with alcohol.

18. Package catheter.

19. Attach label to outside of package. Check accuracy of label.

20. Sterilize catheter with ethylene oxide.

Details of the fabrication steps of the sheath are omitted for brevity and are considered to be within the purview of those of ordinary skill in the art.

While the best mode for carrying out the invention has been described in detail, those familiar with the art to which this invention relates will recognize various alternative designs and embodiments for practicing the invention as defined by the following claims.

What is claimed is:

1. A method for making a laser balloon catheter having an elongated flexible tube with an inflatable balloon connected to the tube, means for inflating and deflating the balloon, a central channel disposed within the balloon and coupled to the tube, an optical fiber with a diffusing tip at its distal end for delivering laser radiation through the balloon to tissue to be treated, the method comprising the steps of:

etching the distal end of the optical fiber to form an etched portion thereof;

cladding the etched portion with an adhesive translucent medium which secures the optical fiber to the central channel so that the optical fiber is eccentrically positioned in relation to the central channel; and applying to the medium a coating which surrounds the central channel, the coating having suspended therewithin a plurality of microballoons for diffusing the laser radiation radially from the optical fiber, so that a cylindrical pattern of diffused laser energy is formed about a predetermined axial length of the central channel.

2. The method of claim 1 wherein the step of etching the distal end of the optical fiber comprises etching a portion of about 7 millimeters in length.

3. The method of claim 1 wherein the step of etching the distal end of the optical fiber comprises the step of etching in hydrofluoric acid.

4. The method of claim 1 wherein the step of cladding the etched portion with an adhesive translucent medium comprises the step of cladding with an epoxy.

5. The method of claim 1 wherein the step of applying a coating to the medium is performed after curing the adhesive translucent medium.

6. The method of claim 1 wherein the microballoons are glass and have an average outside diameter of 0.001 inches and a wall thickness of about 0.0001–0.0002 inches.

7. A method for making a laser balloon catheter having an elongated flexible tube with an inflatable balloon connected to the tube, means for inflating the balloon, means for deflating the balloon, a central channel disposed within the balloon and coupled to the tube, an optical fiber with a diffusing tip at its distal end for delivering laser radiation through the balloon to tissue to be treated, the method comprising the steps of:

etching the distal end of the optical fiber to form an etched portion thereof;

caddying the etched portion with an adhesive translucent medium which secures the optical fiber to the central channel so that the optical fiber is eccentrically positioned in relation to the central channel, the medium having suspended therewithin a plurality of microballoons for diffusing the laser radiation radially from the optical fiber, so that a cylindrical pattern of diffused laser energy is formed about the central channel while substantially avoiding excessive axial propagation and heating of blood distal to the balloon.

8. The method of claim 7 wherein the mass of microballoons is less than 10 micrograms.

9. A laser balloon catheter comprising:

an elongated flexible tube having a distal end and a proximal end;

an inflatable balloon secured to the flexible tube proximate the distal end;

means for inflating and deflating the balloon;

a central channel disposed int eh balloon and coupled to the flexible tube;

an optical fiber mounted eccentrically in relation to the central channel for delivering laser radiation through the tube and balloon to tissue to be treated; and a diffusing tip located at the distal end of the optical fiber for directing laser radiation radially though the balloon, the diffusing tip being located within the balloon between the central channel and the balloon surface and including microballoons for limiting eclipsing of the laser radiation by the central channel and for forming a cylindrical pattern of diffused laser energy about the central channel.

10. The laser balloon catheter of claim 9 wherein the microballoons which surround the central channel and the distal end of the optical fiber direct laser radiation radially outwardly from the central channel.

11. The laser balloon catheter of claim 9 wherein the inflatable balloon is made of PET.

12. The laser balloon catheter of claim 9 wherein the inflatable balloon is made of a high density polyethylene.

13. The laser balloon catheter of claim 9 wherein the inflatable balloon is made of nylon.

14. The laser balloon catheter of claim 10 including a radio opaque layer disposed on an outer surface of the central channel for reflecting laser radiation.

15. A method for making a laser balloon catheter having an elongated tube with an inflatable balloon connected to the tube, means for inflating and deflating the balloon, a central channel disposed within the balloon and coupled to the tube, an optical fiber with a diffusing tip at its distal end for delivering the laser radiation through the balloon to tissue to be treated, the method comprising the steps of:

etching the distal end of the optical fiber to form an etched portion thereof;

applying a layer of a paste to the etched portion of the optical fiber for scattering the laser radiation in a radial direction;

sandwiching the optical fiber between two layers of tubing, an outer layer of which is heat shrinkable; and heat shrinking the outer layer, thereby embedding the optical fiber in the layers of tubing so that the optical fiber is eccentrically positioned in relation to the central channel, and thereby diffusing the laser radiation radially from the optical fiber, so that a cylindrical pattern of diffused laser energy is formed about the central channel while substantially avoiding excessive axial propagation and heating of blood distal to the balloon.

16. The method of claim 15 wherein the optical fiber is a silica fiberoptic.

17. The method of claim 15 wherein the paste is a fluoropolymer paste to provide a relatively high transmission of ultraviolet radiation.

18. The method of claim 15 wherein the tubing is a thin-walled fluoropolymer tubing to provide a relatively high transmission of ultraviolet radiation.

19. The method of claim 15 wherein the laser radiation diffused radially from the optical fiber includes more than 50% of radiation in the UV range.

20. The method of claim 15 wherein the step of sandwiching the fiberoptic between two layers of tubing comprises the step of recladding the etched portion with a fluoropolymer, thereby conferring increased mechanical strength and a reduction in brittleness to the optical fiber.

21. The laser balloon catheter of claim 9 further comprising a plurality of optical fibers for delivering laser radiation through the tube and balloon to tissue to be treated, the plurality of optical fibers being distributed around a circumference of the central channel.

* * * * *